US008389043B2

(12) United States Patent
Speck et al.

(10) Patent No.: US 8,389,043 B2
(45) Date of Patent: *Mar. 5, 2013

(54) PREPARATION FOR RESTENOSIS PREVENTION

(75) Inventors: Ulrich Speck, Berlin (DE); Bruno Scheller, Saarbrucken (DE)

(73) Assignee: Bayer Pharma Aktiengesellschaft, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/835,420

(22) Filed: Jul. 13, 2010

(65) Prior Publication Data

US 2010/0278997 A1  Nov. 4, 2010

Related U.S. Application Data

(62) Division of application No. 11/763,125, filed on Jun. 14, 2007, now abandoned, which is a division of application No. 10/472,844, filed as application No. PCT/DE01/04782 on Dec. 20, 2001, now Pat. No. 7,750,041.

(30) Foreign Application Priority Data

Mar. 26, 2001 (DE) .................. 101 15 740

(51) Int. Cl.
*B05D 3/02* (2006.01)
*A61M 31/00* (2006.01)
*A61M 25/10* (2006.01)

(52) U.S. Cl. ....... 427/2.24; 427/2.1; 427/2.25; 604/509; 604/103.08; 604/265; 604/266

(58) Field of Classification Search .................. 427/2.1, 427/2.24, 2.25; 623/1.42, 1.44, 1.46; 604/103.8, 604/265, 266, 509
See application file for complete search history.

(56) References Cited

U.S. PATENT DOCUMENTS

| 4,101,984 | A | 7/1978 | MacGregor |
|---|---|---|---|
| 4,217,894 | A | 8/1980 | Franetzki et al. |
| 4,247,352 | A | 1/1981 | Stupp et al. |
| 4,305,926 | A | 12/1981 | Everse et al. |
| 4,343,788 | A | 8/1982 | Mustacich et al. |
| 4,364,921 | A | 12/1982 | Speck et al. |
| 4,476,590 | A | 10/1984 | Scales et al. |
| 4,479,795 | A | 10/1984 | Mustacich et al. |
| 4,502,159 | A | 3/1985 | Woodroof et al. |
| 4,532,315 | A | 7/1985 | Letoffe et al. |
| 4,573,476 | A | 3/1986 | Ruiz et al. |
| 4,677,143 | A | 6/1987 | Laurin et al. |
| 4,769,013 | A | 9/1988 | Lorenz et al. |
| 4,776,337 | A | 10/1988 | Palmaz et al. |
| 4,793,825 | A | 12/1988 | Benjamin et al. |
| 4,872,867 | A | 10/1989 | Joh |
| 4,879,135 | A | 11/1989 | Greco et al. |
| 4,886,062 | A | 12/1989 | Wiktor |
| 4,909,799 | A | 3/1990 | Thulesius et al. |
| 4,917,686 | A | 4/1990 | Bayston et al. |
| 4,925,668 | A | 5/1990 | Khan et al. |
| 4,950,256 | A | 8/1990 | Luther et al. |
| 4,994,047 | A | 2/1991 | Walker et al. |
| 4,997,643 | A | 3/1991 | Partain et al. |
| 5,004,461 | A | 4/1991 | Wilson et al. |
| 5,019,096 | A | 5/1991 | Fox, Jr. et al. |
| 5,019,393 | A | 5/1991 | Ito et al. |
| 5,019,601 | A | 5/1991 | Allen |
| 5,051,257 | A | 9/1991 | Pietronigro |
| 5,053,048 | A | 10/1991 | Pinchuk |
| 5,059,166 | A | 10/1991 | Fischell et al. |
| 5,067,491 | A | 11/1991 | Taylor et al. |
| 5,098,977 | A | 3/1992 | Frautschi et al. |
| 5,102,402 | A * | 4/1992 | Dror et al. ..................... 604/265 |
| 5,108,424 | A | 4/1992 | Hoffman et al. |
| 5,112,457 | A | 5/1992 | Marchant |
| 5,135,516 | A | 8/1992 | Sahatjian et al. |
| 5,157,049 | A | 10/1992 | Haugwitz et al. |
| 5,163,952 | A | 11/1992 | Froix et al. |
| 5,165,952 | A | 11/1992 | Solomon et al. |
| 5,171,217 | A | 12/1992 | March |
| 5,176,626 | A | 1/1993 | Soehendra et al. |
| 5,182,317 | A | 1/1993 | Winters et al. |
| 5,197,977 | A | 3/1993 | Hoffman et al. |
| 5,217,493 | A | 6/1993 | Raad et al. |

(Continued)

FOREIGN PATENT DOCUMENTS

| CA | 2132936 | 3/1995 |
|---|---|---|
| CA | 2 207 025 | 6/1996 |

(Continued)

OTHER PUBLICATIONS

Charles et al. "Ceramide-coated balloon catheters limit neointimal hyperplasia after stretch injury in Cartoid arteries" Journal of the Americal Heart Association. Circulation Research. 87, 2000. pp. 282-288.*

(Continued)

*Primary Examiner* — Timothy Meeks
*Assistant Examiner* — Cachet Sellman
(74) *Attorney, Agent, or Firm* — Millen, White, Zelano & Branigan, P.C.

(57) ABSTRACT

The invention relates to a preparation for restenosis prevention. The preparations for restenosis prevention known as yet do not reach sufficient active agent concentrations in the affected sections of the vascular walls as higher doses cause undesirable side effects. The present invention is a preparation to which at least one antihyperplastic agent is added that has a distribution ratio between butanol and water .gtoreq.0.5. The lipophilic active agent is absorbed by the vascular wall fast and in sufficient quantity. The preparation may be a liquid that can pass through capillaries and may contain a contrast agent so that the active agent is transferred into the vascular wall without any additional effort while the usually required contrast radiograms are taken. The preparation may also be applied to a catheter.

37 Claims, No Drawings

U.S. PATENT DOCUMENTS

| | | |
|---|---|---|
| 5,222,971 A | 6/1993 | Willard et al. |
| 5,229,172 A | 7/1993 | Cahalan et al. |
| 5,232,685 A | 8/1993 | Speck et al. |
| 5,234,456 A | 8/1993 | Silvestrini |
| 5,244,654 A | 9/1993 | Narayanan |
| 5,282,823 A | 2/1994 | Schwartz et al. |
| 5,288,711 A | 2/1994 | Mitchell et al. |
| 5,298,255 A | 3/1994 | Sawamoto et al. |
| 5,304,121 A | 4/1994 | Sahatjian |
| 5,306,286 A | 4/1994 | Stack et al. |
| 5,314,688 A | 5/1994 | Kauffman et al. |
| 5,320,634 A | 6/1994 | Vigil et al. |
| 5,342,348 A | 8/1994 | Kaplan |
| 5,344,411 A | 9/1994 | Domb et al. |
| 5,344,444 A | 9/1994 | Glastra |
| 5,345,933 A | 9/1994 | Peterson et al. |
| 5,348,873 A | 9/1994 | Matsunda et al. |
| 5,356,433 A | 10/1994 | Rowland et al. |
| 5,370,614 A | 12/1994 | Amundson et al. |
| 5,380,299 A | 1/1995 | Fearmot et al. |
| 5,383,927 A | 1/1995 | De Golcoechea et al. |
| 5,383,928 A | 1/1995 | Scott et al. |
| 5,419,760 A | 5/1995 | Narciso, Jr. |
| 5,443,458 A | 8/1995 | Eury |
| 5,447,724 A | 9/1995 | Helmus et al. |
| 5,449,382 A | 9/1995 | Dayton et al. |
| 5,454,886 A | 10/1995 | Burrell et al. |
| 5,455,040 A | 10/1995 | Marchant |
| 5,456,663 A | 10/1995 | Lemelson |
| 5,457,113 A | 10/1995 | Cillinan et al. |
| 5,464,450 A | 11/1995 | Buscemi et al. |
| 5,464,650 A | 11/1995 | Berg et al. |
| 5,500,013 A | 3/1996 | Buscemi et al. |
| 5,504,102 A | 4/1996 | Agharkar et al. |
| 5,510,330 A | 4/1996 | Martin et al. |
| 5,531,716 A | 7/1996 | Luzio et al. |
| 5,534,288 A | 7/1996 | Gruskin et al. |
| 5,554,181 A | 9/1996 | Das |
| 5,554,182 A | 9/1996 | Dinh et al. |
| 5,559,448 A | 9/1996 | Koenig et al. |
| 5,567,495 A | 10/1996 | Modak et al. |
| 5,569,463 A | 10/1996 | Helmus et al. |
| 5,571,086 A | 11/1996 | Kaplan et al. |
| 5,578,075 A | 11/1996 | Dayton |
| 5,605,696 A | 2/1997 | Eury et al. |
| 5,607,463 A | 3/1997 | Schwartz et al. |
| 5,607,475 A | 3/1997 | Cahalan et al. |
| 5,609,629 A | 3/1997 | Fearmot et al. |
| 5,624,411 A | 4/1997 | Tuch |
| 5,626,562 A | 5/1997 | Castro |
| 5,629,008 A | 5/1997 | Lee |
| 5,629,881 A | 5/1997 | Leeb et al. |
| 5,643,580 A | 7/1997 | Subramaniam et al. |
| 5,649,977 A | 7/1997 | Campbell et al. |
| 5,674,192 A | 10/1997 | Sahatjian |
| 5,679,400 A | 10/1997 | Tuch |
| 5,681,846 A | 10/1997 | Trissel |
| 5,693,014 A | 12/1997 | Abele et al. |
| 5,697,967 A | 12/1997 | Dinh et al. |
| 5,716,981 A | 2/1998 | Hunter et al. |
| 5,733,327 A | 3/1998 | Igaki et al. |
| 5,762,638 A | 6/1998 | Shikani et al. |
| 5,766,158 A | 6/1998 | Opolski |
| 5,770,198 A | 6/1998 | Coller et al. |
| 5,772,640 A | 6/1998 | Modak et al. |
| 5,789,018 A | 8/1998 | Engelson et al. |
| 5,792,158 A | 8/1998 | Lary |
| 5,814,301 A | 9/1998 | Klopp |
| 5,820,607 A | 10/1998 | Tcholakian et al. |
| 5,824,049 A | 10/1998 | Ragheb et al. |
| 5,827,289 A | 10/1998 | Reiley |
| 5,837,008 A | 11/1998 | Berg et al. |
| 5,863,745 A | 1/1999 | Fitzgerald et al. |
| 5,873,904 A | 2/1999 | Ragheb et al. |
| 5,886,026 A | 3/1999 | Hunter et al. |
| 5,893,867 A * | 4/1999 | Bagaoisan et al. ............ 606/198 |
| 5,902,283 A | 5/1999 | Darouiche et al. |
| 5,916,596 A | 6/1999 | Desai et al. |
| 5,921,952 A | 7/1999 | Desmond, III et al. |
| 5,922,754 A | 7/1999 | Burchett et al. |
| 5,954,706 A | 9/1999 | Sahatjian |
| 5,977,163 A | 11/1999 | Li et al. |
| 5,980,972 A | 11/1999 | Ding |
| 5,981,568 A | 11/1999 | Kunz et al. |
| 5,997,162 A | 12/1999 | English et al. |
| 6,010,480 A | 1/2000 | Abele et al. |
| 6,013,092 A | 1/2000 | Dehdashtian et al. |
| 6,017,948 A | 1/2000 | Rubinfeld et al. |
| 6,039,721 A | 3/2000 | Johnson et al. |
| 6,071,285 A | 6/2000 | Lashinski et al. |
| 6,096,070 A | 8/2000 | Ragheb et al. |
| 6,123,923 A | 9/2000 | Unger et al. |
| 6,146,358 A | 11/2000 | Rowe et al. |
| 6,171,232 B1 | 1/2001 | Papadreau et al. |
| 6,177,061 B1 | 1/2001 | Klaveness et al. |
| 6,203,487 B1 | 3/2001 | Consigny |
| 6,203,551 B1 | 3/2001 | Wu et al. |
| 6,207,133 B1 | 3/2001 | Reszka et al. |
| 6,214,333 B1 | 4/2001 | Zoldhelyi et al. |
| 6,221,467 B1 | 4/2001 | Nazarova et al. |
| 6,231,615 B1 | 5/2001 | Preissman et al. |
| 6,240,616 B1 | 6/2001 | Yan |
| 6,248,100 B1 | 6/2001 | de Toledo et al. |
| 6,258,108 B1 | 7/2001 | Lary |
| 6,264,624 B1 | 7/2001 | Desmond et al. |
| 6,264,642 B1 | 7/2001 | Kuen et al. |
| 6,273,908 B1 | 8/2001 | Ndondo-Lay |
| 6,273,913 B1 | 8/2001 | Wright et al. |
| 6,287,285 B1 | 9/2001 | Michal et al. |
| 6,299,604 B1 | 10/2001 | Ragheb et al. |
| 6,306,151 B1 | 10/2001 | Lary et al. |
| 6,306,166 B1 | 10/2001 | Barry et al. |
| 6,335,029 B1 | 1/2002 | Kamath et al. |
| 6,355,058 B1 * | 3/2002 | Pacetti et al. ............... 623/1.15 |
| 6,364,856 B1 | 4/2002 | Ding et al. |
| 6,369,039 B1 | 4/2002 | Palasis |
| 6,375,931 B2 | 4/2002 | Ostensen et al. |
| 6,400,448 B1 | 6/2002 | Sugawara et al. |
| 6,406,754 B2 | 6/2002 | Chappa et al. |
| 6,419,692 B1 | 7/2002 | Yang |
| 6,479,033 B1 | 11/2002 | Reszka et al. |
| 6,491,619 B1 | 12/2002 | Trauthen et al. |
| 6,491,938 B2 | 12/2002 | Kunz et al. |
| 6,495,579 B1 * | 12/2002 | Hunter ......................... 514/365 |
| 6,500,341 B2 | 12/2002 | Wang et al. |
| 6,503,954 B1 | 1/2003 | Bhat et al. |
| 6,515,016 B2 | 2/2003 | Hunter |
| 6,544,223 B1 | 4/2003 | Kokish et al. |
| 6,544,544 B2 | 4/2003 | Hunter et al. |
| 6,562,024 B2 | 5/2003 | Alvarez de Toledo et al. |
| 6,575,888 B2 * | 6/2003 | Zamora et al. .................... 600/3 |
| 6,585,765 B1 | 7/2003 | Hossainy et al. |
| 6,599,275 B1 | 7/2003 | Fischer et al. |
| 6,599,448 B1 | 7/2003 | Ehrhard et al. |
| 6,599,928 B2 | 7/2003 | Kunz et al. |
| 6,616,591 B1 | 9/2003 | Teoh et al. |
| 6,616,650 B1 | 9/2003 | Rowe |
| 6,635,082 B1 * | 10/2003 | Hossainy et al. ............ 623/1.15 |
| 6,638,913 B1 | 10/2003 | Speck et al. |
| 6,682,545 B1 | 1/2004 | Kester |
| 6,682,546 B2 | 1/2004 | Amplatz |
| 6,695,811 B2 | 2/2004 | Sansom et al. |
| 6,706,892 B1 | 3/2004 | Ezrin et al. |
| 6,730,064 B2 | 5/2004 | Ragheb et al. |
| 6,774,278 B1 | 8/2004 | Ragheb et al. |
| 6,867,190 B2 | 3/2005 | Carney et al. |
| 6,918,927 B2 | 7/2005 | Bates et al. |
| 7,060,051 B2 | 6/2006 | Palasis et al. |
| 7,179,251 B2 | 2/2007 | Palasis et al. |
| 7,419,683 B2 | 9/2008 | Szebeni et al. |
| 7,445,792 B2 | 11/2008 | Toner et al. |
| 7,491,234 B2 | 2/2009 | Palasis et al. |
| 7,611,532 B2 | 11/2009 | Bates et al. |
| 7,731,685 B2 | 6/2010 | Ragheb et al. |
| 7,750,041 B2 | 7/2010 | Speck et al. |
| 7,811,622 B2 | 10/2010 | Bates et al. |
| 2001/0014717 A1 | 8/2001 | Hossainy et al. |

| | | | | | | |
|---|---|---|---|---|---|---|
| 2001/0034363 A1 | 10/2001 | Li et al. | | EP | 1140273 B1 | 10/2001 |
| 2001/0037140 A1 | 11/2001 | Gaudoin et al. | | EP | 1 159 974 | 12/2001 |
| 2001/0044651 A1* | 11/2001 | Steinke et al. ............. 623/1.16 | | EP | 1 250 166 | 10/2002 |
| 2002/0013549 A1 | 1/2002 | Zhong et al. | | EP | 1 372 737 B1 | 1/2004 |
| 2002/0032414 A1 | 3/2002 | Ragheb et al. | | EP | 1 447 098 | 8/2004 |
| 2002/0037358 A1* | 3/2002 | Barry et al. ................. 427/2.1 | | EP | 1 512 398 | 3/2005 |
| 2002/0098278 A1 | 7/2002 | Bates et al. | | EP | 1 521 603 | 4/2005 |
| 2002/0123505 A1 | 9/2002 | Mollison et al. | | EP | 1 536 850 | 6/2005 |
| 2002/0193828 A1 | 12/2002 | Griffin et al. | | EP | 1 666 070 | 6/2006 |
| 2003/0007944 A1 | 1/2003 | O'Halloran et al. | | EP | 1 669 091 | 6/2006 |
| 2003/0028243 A1 | 2/2003 | Bates et al. | | EP | 1 669 092 | 6/2006 |
| 2003/0028244 A1 | 2/2003 | Bates et al. | | EP | 1666071 A1 | 6/2006 |
| 2003/0036794 A1 | 2/2003 | Ragheb et al. | | EP | 1 695 697 | 8/2006 |
| 2003/0059454 A1 | 3/2003 | Barry et al. | | EP | 1 695 698 | 8/2006 |
| 2003/0100600 A1 | 5/2003 | Kinsella et al. | | EP | 1 735 042 | 12/2006 |
| 2003/0195548 A1 | 10/2003 | Kester | | EP | 1 781 209 | 5/2007 |
| 2004/0068241 A1 | 4/2004 | Fischer | | EP | 2 092 941 | 8/2009 |
| 2004/0073284 A1 | 4/2004 | Bates et al. | | EP | 2 092 942 | 8/2009 |
| 2004/0115228 A1 | 6/2004 | Costa et al. | | EP | 2 098 230 | 9/2009 |
| 2004/0224003 A1 | 11/2004 | Schultz | | JP | 06 063145 | 3/1994 |
| 2004/0243225 A1 | 12/2004 | Ragheb et al. | | JP | 7500585 | 1/1995 |
| 2005/0042295 A1 | 2/2005 | Hunter et al. | | JP | 07 328124 | 12/1995 |
| 2005/0063926 A1 | 3/2005 | Bathina et al. | | JP | 10 509691 | 9/1998 |
| 2005/0101522 A1 | 5/2005 | Speck et al. | | JP | 10509691 | 9/1998 |
| 2005/0123605 A1 | 6/2005 | Hunter et al. | | JP | 11012160 A | 1/1999 |
| 2005/0222677 A1 | 10/2005 | Bates et al. | | JP | 2000 507930 | 6/2000 |
| 2005/0250672 A9 | 11/2005 | Speck | | JP | 2001-508320 | 6/2001 |
| 2005/0278021 A1 | 12/2005 | Bates et al. | | JP | 2002-536058 | 10/2002 |
| 2006/0020243 A1 | 1/2006 | Speck et al. | | WO | WO-90 13293 | 11/1990 |
| 2006/0020331 A1 | 1/2006 | Bates et al. | | WO | WO 90/13293 | 11/1990 |
| 2007/0128118 A1 | 6/2007 | Yu et al. | | WO | WO-90 13332 | 11/1990 |
| 2008/0010234 A1 | 1/2008 | Nakagawa et al. | | WO | WO 90/13332 | 11/1990 |
| 2008/0012034 A1 | 1/2008 | Thielen et al. | | WO | WO-91 12779 | 9/1991 |
| 2008/0102033 A1 | 5/2008 | Speck et al. | | WO | WO 91/12779 | 9/1991 |
| 2008/0102034 A1 | 5/2008 | Speck et al. | | WO | WO 92/11890 A1 | 7/1992 |
| 2008/0118544 A1 | 5/2008 | Wang et al. | | WO | WO 92/11896 | 7/1992 |
| 2008/0175887 A1 | 7/2008 | Wang et al. | | WO | WO-92 11896 | 7/1992 |
| 2008/0255508 A1 | 10/2008 | Wang et al. | | WO | WO-92 12717 | 8/1992 |
| 2008/0255509 A1 | 10/2008 | Wang et al. | | WO | WO 92/12717 | 8/1992 |
| 2008/0255510 A1 | 10/2008 | Wang et al. | | WO | WO 92/15282 | 9/1992 |
| | | | | WO | WO 92/20718 | 11/1992 |
| | FOREIGN PATENT DOCUMENTS | | | WO | WO-92 20718 | 11/1992 |
| | | | | WO | WO-93/06792 | 4/1993 |
| CA | 2 218 103 | 10/1996 | | WO | WO 93/06792 | 4/1993 |
| CA | 2345729 | 4/2000 | | WO | WO 93/07875 | 4/1993 |
| CA | 2345697 | 5/2000 | | WO | WO 93/09762 | 5/1993 |
| CN | 1224622 A | 8/1999 | | WO | WO-93 09762 | 5/1993 |
| DE | 4225553 C1 | 5/1994 | | WO | WO 93/09765 | 5/1993 |
| DE | 4446694 | 12/1994 | | WO | WO-93 09765 | 5/1993 |
| DE | 4 334 272 | 4/1995 | | WO | WO 93/11120 | 6/1993 |
| DE | 43 34 272 | 4/1995 | | WO | WO-93 11120 | 6/1993 |
| DE | 4341478 A1 | 6/1995 | | WO | WO 93/11668 | 6/1993 |
| DE | 44 35 652 | 4/1996 | | WO | WO-93 11668 | 6/1993 |
| DE | 195 14 104 | 11/1996 | | WO | WO 94/07484 | 4/1994 |
| DE | 69119753 | 1/1997 | | WO | WO 94/07529 | 4/1994 |
| DE | 69403966 | 2/1998 | | WO | WO-94 07529 | 4/1994 |
| DE | 19724796 A1 | 12/1998 | | WO | WO-94 16706 | 8/1994 |
| DE | 10115740 | 10/2002 | | WO | WO 94/16706 | 8/1994 |
| DE | 10244847.7 | 11/2002 | | WO | WO 94/23787 A1 | 10/1994 |
| DE | 69925936 | 7/2005 | | WO | WO 94/25020 | 11/1994 |
| DE | 20 122 736 | 7/2007 | | WO | WO-94 25020 | 11/1994 |
| EP | 0 357 003 | 3/1990 | | WO | WO-94 26291 | 11/1994 |
| EP | 0 470 246 | 2/1992 | | WO | WO 94/26291 | 11/1994 |
| EP | 0706376 | 7/1993 | | WO | WO 95/03036 | 2/1995 |
| EP | 0 578 998 | 1/1994 | | WO | WO-95 03036 | 2/1995 |
| EP | 0 604 022 | 6/1994 | | WO | WO 95/03083 | 2/1995 |
| EP | 0 623 354 | 11/1994 | | WO | WO 95/03795 | 2/1995 |
| EP | 0 673 114 | 9/1995 | | WO | WO 95/15782 A1 | 6/1995 |
| EP | 0 681 475 | 11/1995 | | WO | WO 96/17629 | 6/1996 |
| EP | 0 717 041 | 6/1996 | | WO | WO 96/20718 A2 | 7/1996 |
| EP | 0 747 069 | 12/1996 | | WO | WO 96/25176 | 8/1996 |
| EP | 0706376 B1 | 6/1997 | | WO | WO 96/25176 A1 | 8/1996 |
| EP | 0 797 988 | 10/1997 | | WO | WO 96/25282 | 8/1996 |
| EP | 0 975 340 | 2/2000 | | WO | WO-96 25282 | 8/1996 |
| EP | 1 407 786 | 4/2000 | | WO | WO 96/38183 | 12/1996 |
| EP | 0 551 182 B1 | 7/2000 | | WO | WO 96/39949 A1 | 12/1996 |
| EP | 1 037 605 | 9/2000 | | WO | WO 96/39970 A1 | 12/1996 |
| EP | 0829238 B1 | 9/2000 | | WO | WO-97 01327 | 1/1997 |
| EP | 1 090 637 | 4/2001 | | WO | WO 97/01327 | 1/1997 |
| EP | 1118325 B1 | 7/2001 | | | | |

| | | |
|---|---|---|
| WO | WO 97/17098 A1 | 5/1997 |
| WO | WO 97/26862 | 7/1997 |
| WO | WO 97/31674 | 9/1997 |
| WO | WO-97 31674 | 9/1997 |
| WO | WO 97/33552 | 9/1997 |
| WO | WO-97 33552 | 9/1997 |
| WO | WO-97 41916 | 11/1997 |
| WO | WO 97/41916 | 11/1997 |
| WO | WO 98/11933 A1 | 3/1998 |
| WO | WO 98/14174 A1 | 4/1998 |
| WO | WO 98/15282 A1 | 4/1998 |
| WO | WO 98/24427 | 6/1998 |
| WO | WO 98/25176 A1 | 6/1998 |
| WO | WO 98/30249 A2 | 7/1998 |
| WO | WO 98/31415 | 7/1998 |
| WO | WO-98 31415 | 7/1998 |
| WO | WO 0006152 | 7/1998 |
| WO | WO 98/36784 | 8/1998 |
| WO | WO-98 43618 | 10/1998 |
| WO | WO 98/43618 A2 | 10/1998 |
| WO | WO 98/47540 A1 | 10/1998 |
| WO | WO 9843618 | 10/1998 |
| WO | WO-99 08729 | 2/1999 |
| WO | WO 99/09729 | 2/1999 |
| WO | WO-99 09729 | 2/1999 |
| WO | WO 99/12577 A1 | 3/1999 |
| WO | WO 99/13916 A2 | 3/1999 |
| WO | WO 99/19004 A2 | 4/1999 |
| WO | WO 99/08729 | 5/1999 |
| WO | WO-99 08729 | 5/1999 |
| WO | WO-99 25336 | 5/1999 |
| WO | WO 99/25336 | 5/1999 |
| WO | WO-99 30684 | 6/1999 |
| WO | WO 99/30684 | 6/1999 |
| WO | WO 99/55396 A1 | 11/1999 |
| WO | WO-99 59556 | 11/1999 |
| WO | WO 99/59556 | 11/1999 |
| WO | WO 99/62510 | 12/1999 |
| WO | WO-00 00023 | 1/2000 |
| WO | WO 00/00023 | 1/2000 |
| WO | WO 00/00238 | 1/2000 |
| WO | WO-00 00238 | 1/2000 |
| WO | WO 00/10552 | 3/2000 |
| WO | WO 00/21584 | 4/2000 |
| WO | WO 00/21584 A1 | 4/2000 |
| WO | WO 00/32238 A1 | 6/2000 |
| WO | WO 00/32267 A2 | 6/2000 |
| WO | WO 00/44414 A1 | 8/2000 |
| WO | WO 00/45744 | 8/2000 |
| WO | WO 00/47197 | 8/2000 |
| WO | WO-00 47197 | 8/2000 |
| WO | WO 00/50105 A2 | 8/2000 |
| WO | WO 01/24866 | 4/2001 |
| WO | WO-01 24866 | 4/2001 |
| WO | WO 01/49338 A1 | 7/2001 |
| WO | WO-01 54748 | 8/2001 |
| WO | WO 01/54748 | 8/2001 |
| WO | WO-01 76525 | 10/2001 |
| WO | WO 01/76525 | 10/2001 |
| WO | WO 01/83016 A2 | 11/2001 |
| WO | WO 02/076509 A2 | 12/2001 |
| WO | WO 02066092 | 8/2002 |
| WO | WO 02/076509 A2 | 10/2002 |
| WO | WO-03 022264 | 3/2003 |
| WO | WO 03/022264 | 3/2003 |
| WO | WO 03/026718 A1 | 4/2003 |
| WO | WO 03/041686 | 5/2003 |
| WO | WO-03 041686 | 5/2003 |
| WO | WO 03/048166 | 6/2003 |
| WO | WO 2004/006976 | 1/2004 |
| WO | WO-2004 006976 | 1/2004 |
| WO | WO 2004/022124 | 3/2004 |
| WO | WO-2004 022124 | 3/2004 |
| WO | WO 2004/028582 A1 | 4/2004 |
| WO | WO 2004/028610 A2 | 4/2004 |
| WO | WO 2005/089855 | 9/2005 |
| WO | WO-2005 089855 | 9/2005 |
| WO | WO-2005 112570 | 12/2005 |
| WO | WO 2005/112570 | 12/2005 |
| WO | WO 2006/023104 | 3/2006 |
| WO | WO-2006 023104 | 3/2006 |
| WO | WO 2008/063576 | 5/2008 |
| WO | WO-2008 063576 | 5/2008 |
| WO | WO 2009/051614 | 4/2009 |
| WO | WO-2009 051614 | 4/2009 |
| WO | WO-2009 051615 | 4/2009 |
| WO | WO 2009/051615 | 4/2009 |
| WO | WO-2009 051616 | 4/2009 |
| WO | WO 2009/051616 | 4/2009 |
| WO | WO 2009/051618 | 4/2009 |
| WO | WO-2009 051618 | 4/2009 |

OTHER PUBLICATIONS

Li et al., J. Nucl. Med., 38 (7), 1042-47 (1997).
Perflorocarbon Compounds as X-Ray Contrast Media in the Lungs Bulletin Soc, Int. Chic. 1975, 34 (2) 137-41.
Paclitaxel: Ein Chemotherapeuticum Zur Restenoseprohylaze? Experimentelle Untersuchengen In Vitro Und In Cico, Zeitschrift Fur Kardiologie, Band 89, Heft 5 (2000), pp. 390-397.
Herdeg et al., J. Am. Coll. Cardiol. 35 1969-1976.
Local Drug Delivery: Impact of Pressure, Substance Characteristics and Stenting on Drug Transfer into the Arterial Wall, Catherization and Cardiovascular Interventions 47; p. 102-106.
Engelmann et al, 2007 International Journal of Pharmaceutics 329, 12-18.
Extracts from the UK Trademarks Register (E7).
Print-out from an online tool for calculating a coefficient of distribution between octanol and water.
Final Rejection dated May 1, 2008 in related U.S. Appl. No. 10/528,577, filed Mar. 21, 2005.
Non-Final Rejection dated Oct. 5, 2007 in related U.S. Appl. No. 10/528,577, filed Mar. 21, 2005.
Non-Final Rejection dated Jul. 2, 2007 in related U.S. Appl. No. 10/472,844, filed Sep. 26, 2003.
Final Rejection dated Nov. 1, 2007 in related U.S. Appl. No. 10/472,844, filed Sep. 26, 2003.
Non-Final Rejection dated May 29, 2008 in related U.S. Appl. No. 10/472,844, filed Sep. 26, 2003.
Final Rejection dated Mar. 4, 2009 in related U.S. Appl. No. 10/472,844, filed Sep. 26, 2003.
Non-Final Rejection dated Jan. 15, 2009 in related U.S. Appl. No. 10/618,977, filed Jul. 14, 2003.
Kolodgie et al., Circulation Research, 2000; 87: 264-267.
Nishio, K., et al., "Enhanced Interaction Between Tubulin and Microtubule-Associated Protein 2 Via Inhibition of Map Kinase and CDC2 Kinase by Paclitaxel," Int. J. Cancer: 63, p. 688-693 (1995).
Ding, A., et al., "Association of Mitogen-Activated Protein Kinase with Microtubules in Mouse Macrophases," J. Exp. Med. vol. 183, Apr. 1996, p. 1899-1904.
Lieu, C.-H., et al., "Role of Mitogen-Activated Protein Kinase in Kinase in Taxol-Induced Apoptosis in Human Leukemic U937 Cells," Cell Growth & Differentiation, vol. 9, p. 767-776, Sep. 1998.
"Ceramide-Coated Balloon Catheters Limit Neointimal Hyperplasia After Stretch Injury in Carotid Arteries," Circulation Research, 2000; 87: 282-288.
Online Extract From Sigma-Aldrich Web Site Concerning Poly Vinyl Alcohol (Molecular Weight: Mw 500).
Online Extract From Sigma-Aldrich Web Site Concerning Poly Vinyl Alcohol (Molecular Weight: Mw 1700).
Online Extract From Sigma-Aldrich Web Site Concerning Poly Acrylic Acid (Molecular Weight: Mw 1800).
Online Extract From MSDS Online Concerning Sucrose.
Online Extract From Polysciences, Inc Web Site Concerning Poly Lactic Acid (Molecular Weight: Mw1600 to 2400).
Online Extract From Polysciences, Inc Web Site Concerning Polyvinylpyrrolidone (Molecular Weight: Mw 2500).
Online Extract From Polysciences, Inc Web Site Concerning Polycaprolactone (Molecular Weight: Mw 2000).
Online Extract From Polysciences, Inc Web Site Concerning Polycaprolactone (Molecular Weight: Mw 1250.
"Stent", www.thefreedictionary.com/stent, 2000.
"The Definition of Coated Stent", www.medterms.com, 2003.

"Balloon Catheter", en.wikipedia.org/wiki/balloon.catheter, 2008.

Werk et al.: "Inhibition of Restenosis in Femoropopliteal Arteries: Paclitaxel-Coated Versus Uncoated Balloon: Femoral Paclitaxel Randomized Pilot Trial", Circulation: Journal of the American Heart Association, 2008, vol. 118, pp. 1358-1365.

Tepe et al.: "Local Delivery of Paclitaxel to Inhibit Restenosis During Angioplasty of the Leg", The New England Journal of Medicine, 2008, vol. 358, No. 7, pp. 689-699.

Henry et al.: "'Poba Plus': Will the Balloon Regain Its Luster?", Circulation: Journal of the American Heart Association, 2008, vol. 118, pp. 1309-1311.

Schwartz et al.: "Preclinical Restenosis Models and Drug-Eluting Stents", Journal of the American College of Cardiology, 2004, vol. 44, No. 7, pp. 1373-1385, Elsevier Inc.

Badapulle et al.: "A Hierarchical Bayesian Meta-Analysis of Randomised Clinical Trials of Drug-Eluting Stents", Lancet, 2004, vol. 364, pp. 583-591.

Scheller et al.: "Treatment of Coronary In-Stent Restenosis With a Paclitaxel-Coated Balloon Catheter", The New England Journal of Medicine, 2006, vol. 355, No. 20, pp. 2113-2124.

Licha et al.: "Hydrophilic Cyanine Dyes as Contrast Agents for Near-Infrared Tumor Imaging: Synthesis, Photophysical Properties and Spectroscopic In Vivo Characterization", Phtochemistry and Photobiology, 2000, vol. 72, No. 3, pp. 392-398.

Phillips et al.: "A-Level Biology", Oxford University Press, 1989, pp. 7-8.

English Translation of DE 4225553 C1.

Opposition of EP1,666,070.

Opposition of EP1,666,071.

Psychyrembel Klinishces Worterbuch.

Pierre Signore et al., "Complete Inhibition of Intimal Hyperplasia by Perivascular Delivery of Paclitaxel in Balloon-injured Rat Carotid Arteries," Laboratory Investigations, vol. 12, No. 1, Jan. 2001, pp. 79-88.

File History of U.S. Appl. No. 60/395,434, filed Jul. 12, 2002.

File History of U.S. Appl. No. 60/244,446, filed Oct. 31, 2000.

Ran Kornowski et al., "Slow-Release Taxol Coated GRIT™ Stents Reduce Neointima Formation in a Porcine Coronary In-Stent Restenosis Model," 70th Scientific Sessions of the American Heart Association, Nov. 9-12, 1997.

Alan W. Heldman et al., "Paclitaxel Stent Coating Inhibits Neointinal Hyperplasia at 4 Weeks in a Porcine Model of Coronary Restenosis," Circulation, May 8, 2001, pp. 2289-2295.

Department of Health and Human Services Notice of Intramural Research Project, Oct. 1, 1993-Sep. 30, 1994; "Molecular Strategies to Treat Restenosis," 4 pp.

Department of Health and Human Services Notice of Intramural Research Project, Oct. 1, 1994-Sep. 30, 1995, "Local Delivery of Therapeutic Agents for the Prevention of Restenosis," 6 pp.

Teruo Inoue et al., "Comparison of Activation Process of Platelets and Neutrophils After Coronary Stent Implantation Versus Balloon Angioplasty for Stable Angina Pectoris," The American Journal of Cardiology, vol. 86, Nov. 15, 2000, pp. 1057-1062.

Eric K. Rowinsky et al., "Paclitaxel (Taxol)", Alastair JJ. Wood, ed. "Drug Therapy," The New England Journal of Medicine, vol. 332, No. 15, Apr. 13, 1995, pp. 1004-1014.

Dorothea I. Axel et al., "Paclitaxel Inhibits Arterial Smooth Muscle Cell Proliferation and Migration In Vitro and In Vivo Using Local Drug Delivery," Circulation, 1997, vol. 96, pp. 636-645.

Bruno Scheller et al., "Acute Cardiac Tolerance of Current Contrast Media and the New Taxane Protaxel Using Iopromide as Carrier During Porcine Coronary Angiography and Stenting," Investigative Radiology, vol. 37, No. 1, pp. 29-34.

International Preliminary Examination Report for PCT/DE2003/002871.

International Preliminary Examination Report for PCT/DE2001/04782.

International Search Report for EP 06 00 1041, Search Date: Apr. 11, 2006.

International Search Report for EP 06 00 1042, Search Date: Apr. 10, 2006.

International Search Report for EP 06 00 1040, Search Date: Apr. 11, 2006.

International Search Report for PCT/DE01/04782, Search Date: Dec. 27, 2002.

International Search Report for PCT/EP03/10480, Search Date: Feb. 20, 2004.

International Search Report for PCT/DE03/02871, Search Date: Feb. 17, 2004.

Speck, Ulrich et al., "Inhibition of Restenosis in Stented Porcine Coronary Arteries," Investigative Radiology, vol. 39 No. 3, Mar. 2004, pp. 182-186.

Scheller, Bruno et al., "Addition of Paclitaxel to Contrast Prevents Restenosis After Coronary Stent Implantation," Journal of the American College of Cardiology, vol. 42 No. 8, 2003, pp. 1415-1420.

Scheller, Bruno et al., "Paclitaxel Balloon Coating, a Novel Method for Prevention and Therapy of Restenosis," Circulation, Aug. 17, 2004, pp. 810-814.

Singla, Anil K. et al., "Paclitaxel and its Formulations," International Journal of Pharmaceutics, vol. 235, 2002, pp. 179-192.

Nuijen, Bastiaan et al., "Progress in the Development of Alternative Pharmaceutical Formulations of Taxanes," Investigational New Drugs, vol. 19, 2001, pp. 143-153.

Wood, Shelly, "Drug-eluting Stents: Where They Are Now," HeartWire, Jan. 22, 2003, 7 pgs., http://www.theheart.org/documents/page.cfm?from=590001500&doc_id=33903.

Singla, AK et al. "Paclitaxel and its formulations," Int.J.Pharmceutics 235 (2002): 179-182.

Nuijen B et al., "Progress in the development of alternative . . . ," Investigational New Drugs, 19(2001): 143-153.

Speck et al., "Inhibition of restenosis in stented porcine coronary . . . " Invest.Radiol. 2004, 39, 182-186.

"Drugeluting stents: Where are they now," Heartwire, p. 2, communication of www.theheart.org, Jan. 22, 2003.

Scheller et al., "Addition of paclitaxel to contrast media prevents restenosis after coronary stent implantation," J.Am.Coll.Radiol. 2003, 42:1415-1420.

Scheller et al., "Paclitaxel balloon cutting—a novel method for prevention and therapy of restenosis," Circulation, 2004, 110:810-814.

"Ceramide-coated balloon catheters limit neointimal hyperplasia after stretch injury in carotid arteries," Circulation Research 2000, 87,282.

Martin Oberhoff et al., "Local delivery of Paclitaxel using the double-ballon perfusion catheter before stenting in the porcine coronary artery," 2001,Catheterization and Cardiovascular Interventions, pp. 562-568, vol. 53.

Christopher J. Creel et al., "Arterial Paclitaxel distribution and deposition," Circulation Research, Apr. 28, 2000, pp. 879-884.

Dr. Karsch, "Lokale Applikation von Paclitaxel mit dem Schneider-Doppelballon," nach experimenteller Stentimplantation an den Koronaraterien des Schweines, Gießen 2001.

Toru Kataoka et al., "7-Hexanoyltaxol-Eluting Stent for prevention of Neointimal Growth," Circulation, Oct. 1, 2002, pp. 1788-1793.

Roger Charles et al., "Ceramide-coated ballon catheters limit neointimal hyperplasia after stretch injury in carotid arteries," Circulation Research, Aug. 18, 2000, pp. 282-288.

Frank D. Kolodgie et al., Local delivery of ceramide for restenosis: Is there a future for lipid therapy? Circulation Research, Aug. 18, 2000, pp. 264-267.

Alan W. Heldman et al., "Paclitaxel stent coating inhibits neointimal hyperplasia at 4 week in a porcine model of coronary restenosis," Circulation, May 8, 2001, pp. 22892295.

Johnathan D. Adams et al., "Taxol: a history of pharmaceutical development and current pharmaceutical concerns," Journal of the National Cancer Institute Monographs, 1993, pp. 141-147, No. 15.

Elsevier Science Publishers, Amsterdam, NL; Jackson D.M. A. et al Current usage of contrast agents, anticoagulant and antiplatelet drugs in angiography and angioplasty in the UK. retrieved from STN Database accession No. 95327068 XP002226116.

Jackson et al., "Current usage of contrast agents, anticoagulant and antiplatelet drugs in angiography and angioplasty in the UK," Clinical Radiology, 1995, pp. 699-704, vol. 50, No. 10.

Judgment of Sep. 16, 2011 (Paper No. 52) from Interference No. 105,787.

Redeclaration of Interference (Paper No. 48) issued Sep. 13, 2011.

Applicants' Amendment of Sep. 12, 2011 (Paper No. 47), filed in U.S. Appl. No. 11/763,125, and cited in the Judgment of Sep. 16, 2011 in Interference No. 105,787.

"Water soluble paclitaxel prodrugs," Espacenet, Publication Date: Jun. 27, 2000; English Abstract of JP-2000 507930.

Buaayu Kk, "Balloon catheter for intravascular dosing," Patent Abstracts of Japan, Publication Date: Mar. 8, 1994; English Abstract of JP-06 063145.

Magna International Toronto, "Process for producing a plastic cladding component and cladding component produced especially by said process," Espacenet, Publication Date: Aug. 22, 1996; English Abstract of WO-96 25282.

Stemberger Axel Dr., "Coating for bio-material to be used e.g. as sutures," Espacenet, Publication Date: Apr. 11, 1996; English Abstract of DE-44 35 652.

Terumo Corp., "Medicine dosing catheter," Patent Abstracts of Japan, Publication Date: Dec. 19, 1995; English Abstract of JP-07 328124.

Thomson Innovation, Patent Record View, Publication Date: Jan. 19, 1995; English abstract of JP-7 500585.

Thomson Innovation, Patent Record View, Publication Date: Sep. 22, 1998; English abstract of JP-10 509691.

Herberts & Co GMBH, "Liquid mixtures of photo-initiators, process for their production and their use," Espacenet, Publication Date: Nov. 26, 1992; English Abstract of WO-92 20718.

Stemberger Axel Dr., "Coating for bio-material to be used e.g. as sutures," Espacenet, Publication Date: Apr. 13, 1995; English Abstract of DE-4 334 272.

Strecker Ernst Peter Dr Med Pr., "Implantable percutaneous endoprosthesis," Espacenet, Publication Date: Jan. 19, 1994; English Abstract of EP-0 578 998.

Atkins, Peter, "Chapter 7: Simple Mixtures," Physical Chemistry, 6th ed., 1997, pp. 176-186.

Barath et al., JACC, 1989, vol. 13, No. 4, pp. 252A.

Bartoli et al., J. Microencapulation, 1990, vol. 7, No. 2, pp. 191-197.

Baron et al., Cardiovascular Research, Jun. 2000, vol. 46, pp. 585-594.

BC Lippold, "Retardarzneiformen" in E. Nurnberg, Hagers Handbuch der pharmazeutischen Praxis, vol. 2, Springer-Verlag Berlin Heidelburg New York, 5$^{th}$ edition, 1991, pp. 832-840.

Brunner, H. et al., "Synthesis and in vitro testing of hematoporphyrin type ligands in platinum (II) complexes as potent cytostatic and phototoxic antitumor agents," Inorganica Chimica Acta, 1997, vol. 264, pp. 67-79.

Bult, H., "Restenosis: a challenge for pharmacology," TIPS, Jul. 2000, vol. 21, pp. 274-279.

Consigny, P. Macke et al., "Local Delivery of an antiproliferative drug with use of hydrogel-coated angioplasty balloons," J. Vasc. Interv. Radiol., 1994, vol. 5, pp. 553-560.

Coomber, B. L. et al., "In vitro endothelial wound repair: Interaction of cell migration and proliferation," Arteriosclerosis, Mar. 1990, vol. 10, No. 2, pp. 215-222.

Cox et al., Coronary Artery Disease, 1992, vol. 3, pp. 237-248.

Cremers et al., "V1742—Paclitaxel-beschictete PTCA-Katheter: Gibt es Unterschiede? Einfluss von PACCOCATH and DIOR Ballonkathetern auf die Neointimaporliferation an Schweinekoronarien," Clin. Res. Cardiol., 1997.

Cremers, B et al., "Comparison of two different paclitaxel-coated balloon catheters in the porcine coronary restenosis model," Clin. Res. Cardiol., 2009, vol. 98, pp. 325-330.

Dichek, D. A. et al., "Seeding of Intravascular stents with genetically engineered endothelial cells," Circulation, 1989, vol. 80, No. 5, pp. 1347-1353.

Dordunoo, S. K. et al., "Release of taxol from poly(ε-caprolactone) pastes: effect of water-soluble additives," Jounral of Controlled Release, 1997, vol. 44, pp. 87-94.

Drachmann et al., "Neoinitimal thickening after stent delivery of paclitaxel: Charge in composition and arrest of growth over six month," J. Am. Coll. Cardiol., 2000, vol. 36, pp. 2325-2332.

Elke M: Kontrastmittel in der radiologischen Diagnostik, pp. 113-119, 3$^{rd}$ edition, Georg Thieme Verlag Stuttgart New York, 1992.

English Translation of Elke M: Kontrastmittel in der radiologischen Diagnostik, pp. 113-119, 3$^{rd}$ edition, Georg Thieme Verlag Stuttgart New York, 1992.

Forth, W. et al. "Allegemeine und spezielle Pharmakologie und Toxikologie," 7 Auflage. Heidelberg: Spektrum Akademischer Verlag, 1996, Chapter, 1, 2, 3.

Garcia-Matinez et al., Acta Anat, 1988, vol. 133, pp. 282-288.

Gershlick et al., "Inhibition of Restenosis with a Paclitaxel-Eluting, Polymer-Free Coronary Stent: The European evaluation of pacliTaxel Eluting Stent (ELUTES) Trail," Circulation, 2004, vol. 109, pp. 487-493.

Gold, Victor et al., "Amount of Substance Concentration," Compendium of Chemical Technology: International Union of Pure and Applied Chemistry Recommendations, 1987, pg. 19.

Grossmann, S, "Neuartige Zubereitungen Hemmung der Neointimaproliferation in verengten Arterien," Dissertation zur Erlangung des akademischen Grades des Doktors der Naturwissenschaften (Dr. rer. nat.), Nov. 2006.

Hamm, C. W. et al., "Guideline: Diagnostic Heart Catheter Examination," Clin Res Cardiol, 2008, vol. 97, pp. 475-512.

English Translation of Hamm, C. W. et al., "Guideline: Diagnostic Heart Catheter Examination," Clin Res Cardiol, 2008, vol. 97, pp. 475-512.

Hiatt, Catheterization and Cardiovascular Interventions, vol. 55, pp. 409-417, 2002.

Hou, D. et al., "Intrapericardial paclitaxel delivery inhibits neointimal proliferation and promotes arterial enlargement after porcine coronary overstretch," Circulation, 2000, vol. 102, pp. 1575-1581.

Indolfi et al., "Smooth Muscle Cell Proliferation Is Proportional to the Degree of Balloon Injury in a Rat Model of Angioplasty," Circulation, 1995, vol. 92, pp. 1230-1235.

Kalbitz et al., "Modulation der Wirkstoffpenetration in die Haut," Pharmazie, 1996, vol. 51, pp. 619-637.

Kandarpa et al., J. Vasc. Inter. Radiol., Nov./Dec. 1997, vol. 8, pp. 997-1004.

Kandarpa et al., J. Vasc. Inter. Radiol., May/Jun. 1998, vol. 9, pp. 487-493.

Katsuda et al., Clin. Ter. Cardiovasc.,1990, IX(4), pp. 245-248.

Khan, I. A. et al., "The Intra-vascular stent as a site-specific local drug delivery system," Drug Development and Industrial Pharmacy, 2005, vol. 31, pp. 59-78.

Kirk-Othmer, Encyclopedia of Chemical Technology, 3$^{rd}$ Edition, vol. 17, 1982, John Wiley & Sons, pp. 281-310.

Lamba, Nina M. K. et al., "Structure and Physical Characterization of Polyurethanes," Polyurethanes in Biomedical Applications ,Ch. 4, pp. 43-52, 1998, CRC Press.

Langer, R., "New methods of drug delivery," Science, Sep. 28, 1990, vol. 249, pp. 1527-1533.

Leo, Albert et al., "Partition Coefficients and Their Uses," Chemical Reviews, Dec. 1971, vol. 71, No. 6, pp. 525-616.

Liggins, Richard T. et al., "Paclitaxel loaded poly(L-lactic acid) microspheres: properties of microspheres made with low molecular weight polymers," International Journal of Pharmaceutics, 2001, vol. 222, pp. 19-33.

Liggins, R. T. et al., J. Pharma. Sci., 1997, vol. 86, pp. 1458-1463.

Lübbe, A. S. et al., "Preclinical experiences with magnetic drug targeting: Tolerance and Efficacy," Cancer Research, 1996, vol. 56, pp. 4694-4701.

Manderson et al., "Balloon Catheter Injury to Rabbit Cartoid Artery. I. Changes in smooth muscle phenotype," Artheriosklerosis, 1989, vol. 9, pp. 289-298.

Matthew, R. T. et al., J. Med. Chem., 1992, vol. 35, pp. 141-151.

Mitchel et al., Circulation, Oct. 1994, vol. 90, pp. 1979-1988.

Mortimer, C. et al., Basiswissen Chemie (excerpt) (1987) (D50).

Muller et al., JACC, 1990, vol. 17, No. 6, pp. 126B-131B.

Nairn, John A., "Polymer Characterization," Materials Science & Engineering 5473, 2003, Ch. 3, pp. 43-55.

Nicolaou, K. C. et al., "Design, synthesis and biological activity of protaxols," Nature, Jul. 29, 1993, vol. 364, pp. 464-466.

Parker, Sybil P., "Micelle," McGraw-Hill Encyclopedia of Chemistry — Second Edition, 1992, pp. 638-639.

Sangster, J. et al., Octanol-Water Partition Coefficients: Fundamentals and Physical Chemistry, 1997, vol. 2 of Wiley Series in Solution Chemistry, pp. 1-49.

Schmitz, S. A. et al., "Superparamagnetic iron oxide-enhanced MRI of atherosclerotic plaques in Watanabe Hereditable Hyperlipidemic Rabbits," Investigative Radiology, Aug. 2000, vol. 35, No. 8, pp. 460-471.
Sharma, U. S. et al., J. Pharma. Sci., 1995, vol. 84, pp. 1223-1230.
Slepian, in textbook of interventional cardiology, 1990, Section IV, Chapter 32, pp. 647-670.
Sollott, Steven J. et al., "Taxol Inhibits Neointimal Smooth Muscle Cell accumulation after angioplasty in the rat," The Journal of clinical Investigation, Apr. 1995, vol. 95, pp. 1869-1876.
Speck, Ulrich — German Priority Document for file No. 101 15 740.1 filed on Mar. 26, 2001.
Swindell, C.S. et al., J. Med. Chem, 1991, vol. 34, pp. 1176-1184.
Tarr, B. D. et al., J. Parent Sci. Technol., 1987, vol. 41, pp. 31-33.
Tawashi, R. "The dissolution rates of crystalline drugs," J. Mond. Pharm. 1968, vol. 4, No. 11, pp. 371-379.
Ulicky, L. et al., "Nernst's Distribution Law," Comprehensive Dictionary of Physical Chemistry, pp. 266-267, 1992.
Van Belle, E. et al., "Passivation of metallic stents after arterial gene transfer of phVEGF165 inhibits thrombus formation and intimal thickening," J. Am. Coll. Cardiol., 1997, vol. 29, pp. 1371-1379.
Voigt, R., Lehrbuch der pharmazeutishchen Technologie, $5^{th}$ edition, VEB Verlag Volk and Gesundheit Berlin, 1984, p. 689.
Voisard et al., Coronary Artery Disease, 1993, vol. 4, pp. 935-942.
Wichert, B et al., "Low Molecular weight PLA: a suitable polymer for pulmonary administered microparticles?" J. Microencapsulation, 1993, vol. 10, No. 2, pp. 195-207.
Yushmanov, Victor E. et al., "Dipyridamole Interacts with the Polar Part of Cationic Reversed Micelles in Chloroform: 1H NMR and ESR Evidence," Journal of Colloid and Interface Science, 1997, vol. 191, pp. 384-390.
Clinical Cardiology Divergent Effects on Coronary Artery Disease: Abstract from $70^{th}$ Scientific Session: Circulation, vol. 96, No. 8, Oct. 21, 2007.
Abstracts From the $70^{th}$ Scientific Sessions, Circulation, Oct. 21, 1997, 96 Suppl. 1: 1-288.
English Abstract of CN 1 224 622, Aug. 4, 1999.
English Abstract of DE 19514104, Stemberger, Axel, Dr., "Coating for bio-material insertable into the bloodstream or tissue of the human body," Nov. 28, 1996.
English Abstract of DE 69925936, Stemberger, Axel, Dr., "High efficiency local drug delivery," May 11, 2006.
English Abstract of DE 4435652, Stemberger, Axel Dr., "Coating for bio-material to be used e.g. as sutures," Apr. 11, 1996.
English Abstract of EP 0 551 182, Morris, R. E. et al., "Method of treating hyperproliferative vascular disease using rapamycin, eventually in combination with mycophenolic acid," Jul. 14, 1993.
English Abstract of JP-06-063145, "Balloon Catheter for intravascular dosing," BUAAYU KK, Patent Abstracts of Japan, Publication Date: Mar. 8, 1994.
English Abstract of JP-06-063145, "Balloon Catheter for Intravascular dosing," BUAAYU KK, Thomson Innovation, Publication Date: Mar. 8, 1994.
English abstract of JP-07-500585, Thomson Innovation, Patent Record View, Publication Date: Jan. 19, 1995.
English Abstract of JP-07-328124, "Medicine dosing catheter," Terumo Corp., Patent Abstracts of Japan, Publication Date: Dec. 19, 1995.
English abstract of JP-10-509691, Thomson Innovation, Patent Record View, Publication Date: Sep. 22, 1998.
English Abstract of JP-11-012160, Jan. 19, 1999.
English Translation of JP 36371777, Thomson Innovation, Publication Date: Mar. 23, 2005.
Patent Family Listing for JP-2001 508320 (Publication Date: Jun. 26, 2001), Thomson Innovation.
Patent Family Listing for JP-2002 536058 (Publication Date: Oct. 29, 2002), Thomson Innovation.
English Abstract of WO 92/20718, Nov. 26, 1992.
English Abstract of WO 96/25282, Kaufmann, G. et al., "Process for producing a plastic cladding component and cladding component produced especially by said process," Aug. 22, 1996.
Office Action issued Apr. 20, 2007 in U.S. Appl. No. 10/618,977, filed Jul. 14, 2003.
Office Action issued Oct. 13, 2011 in U.S. Appl. No. 11/763,116.
Office Action issued Dec. 6, 2011 in U.S. Appl. No. 12/835,414.
Office Action issued Feb. 16, 2012 in U.S. Appl. No. 12/782,989.
U. S. Appl. No. 08/094,536 (Priority of D2), Jul. 19, 1993.
U.S. Appl. No. 08/062,451 (Priority of D3), May 16, 1993.
English translation of Decision of Final Rejection, Japanese Application No. JP 2004-235694, issued Mar. 9, 2010.
Office Action issued Feb. 22, 2010 in U.S. Appl. No. 10/528,577.
Notice of Allowance issued Aug. 23, 2010 in U.S. Appl. No. 10/528,577.
Notice of Allowance issued Dec. 9, 2010 in U.S. Appl. No. 10/528,577.
Notice of Allowance issued Nov. 28, 2011 in U.S. Appl. No. 10/528,577.
Notice of Allowance issued Jun. 25, 2012 in U.S. Appl. No. 10/528,577.
Office Action issued May 25, 2012 in U.S. Appl. No. 12/782,989.
Office Action issued May 23, 2011 in U.S. Appl. No. 12/835,414.
Office Action issued May 9, 2012 in U.S. Appl. No. 12/835,414.
Office Action issued Apr. 29, 2009 in U.S. Appl. No. 11/763,116.
Office Action issued Sep. 18, 2009 in U.S. Appl. No. 11/763,116.
Office Action issued Apr. 8, 2010 in U.S. Appl. No. 11/763,116.
Office Action issued May 7, 2012 in U.S. Appl. No. 11/763,116.

* cited by examiner

PREPARATION FOR RESTENOSIS PREVENTION

This application is a divisional of U.S. application Ser. No. 11/763,125 now abandoned, filed on Jun. 14, 2007, which is incorporated by reference herein, which is a divisional of U.S. application Ser. No. 10/472,844 filed on Sep. 26, 2003 now U.S. Pat. No. 7,750,041, which is the national phase of PCT/DE01/04782 filed on Dec. 20, 2001.

The invention relates to a preparation for restenosis prevention and its application to an angiography catheter.

Stenoses of blood vessels are a major cause of morbidity and mortality. Local stenoses or occlusions of larger vessels up to ca. 2 mm in diameter can be dilated back to their original lumen in many instances using inflatable balloon catheters. High pressures are applied when doing this, which may result in lacerations of the thickened vascular walls that are squeezed and displaced into the surrounding tissue. In some of these operations, tubular perforated metal supports (stents) are implanted to keep the vessels open. The vascular walls treated in this way frequently respond by increased growth in thickness that is similar to developing a scar within a few weeks and months. As a result and due to advancing arteriosclerosis, these vessels may relatively soon become stenosed again (restenosis). Restenosis is a severe medical problem that causes high costs.

A proven clinical method to prevent restenosis is irradiation of the affected vascular wall sections with a high dosage of X-rays (extracorporeal sources or intraluminal radioisotopes) immediately after the surgery Major disadvantages of irradiation are the required precautions when handling preventive radiation dosages. Many other methods for preventing premature restenosis have been tested in labs and clinical practice but as yet without any major breakthrough [Bult H. Restenosis: A challenge for pharmacology. Tips 21 pp. 274-279, 2000]. Good results were only achieved using drug-releasing stents. For this method to be effective, stents have to be implanted so that restenosis cannot be prevented when the vessel is just dilated and no stent is implanted.

Inhibition of mitosis, reactive vascular wall thickening and restenosis has been described for a great number of drugs: Important principles of action are inhibition of platelet aggregation, enzyme inhibition, inhibition of mitosis, cytostatics, and corticoids. Favorable results were achieved in vitro and partly in animal experiments but have not been confirmed in clinical tests. A frequent explanation offered is that active agent concentrations in the affected sections of the vascular wall are insufficient. This is particularly true for oral and intravenous administration where side effects prevent higher doses. As an alternative, administration using specific catheters was attempted wherein these catheters either press the drug solution through the pores of a tight-sitting balloon directly into the vascular wall or block supply and discharge in a vessel section and expose the vessel wall to the drug solution for some time [Herdeg, C., M. Oberhoff, D. I. Siegel-Axel, A. Baumbach, A. Blattner, A. Kuttner, S. Schroder, K. R. Karsch: Paclitaxel: Ein Chemotherapeutikum zur Restenoseprophylaxe? Experimentelle Untersuchungen in vitro und in vivo. Z Kardiol 89 pp. 390-397, 2000]. Drug exposure of previously dilated vessel sections that was effective over a longer period of time was achieved by the slow release of active agents from coated stents. However, the problem of achieving sufficient active agent concentrations over a sufficient exposure time in the vessel sections requiring treatment remains the same with all these methods. Hydrophilic active agents are quickly washed out of tissues [Baumbach, A., C. Herdeg, M. Kluge, M. Oberhoff, M. Lerch, K. K. Haase, C. Wolter, S. Schroder, K. R. Karsch: Local drug delivery: Impact of pressure, substance characteristics, and stenting on drug transfer into the arterial wall. Cathet Cardiovasc Intervent 47 pp. 102-106, 1999]. Repeated administration is impossible because of the invasive access using catheters. Lipophilic active agents do not dissolve well enough in vessel-compatible aqueous media or are kept in solution as micelles or liposomes; these micelles or liposomes are only slowly absorbed by the tissue. Administration using special catheters that interrupt the blood flow for some time or press the active agent solution under high pressure into the vascular wall first of all causes additional tissue damage and intensifies reactive hyperplasia.

Coated, drug-releasing stents are difficult to produce in constant quality, they contain only very low active agent quantities due to their light weight and delicate design and are not suitable for proximal and distal treatment of the vascular sections at risk of restenosis a few millimeters around the stent. If a stent was implanted at an earlier time, and there is stenosis in its lumen, this can be removed by inflating a balloon catheter. This implantation of a second stent into the lumen of the first stent to prevent vessel wall hyperplasia as a consequence of dilatation is undesirable so that there is no effective method of restenosis prevention for this case. The same applies when there is no indication for implanting a stent after angioplasty or when hyperplastic vessel processes are taking place without clear stenosis of the lumen so that neither vessel dilatation nor stent implantation are required. Some of these vessel wall changes may cause sudden, mostly thrombotic occlusions. In this case, too, a method independent of stent implantation for inhibiting pathological vessel wall changes is desirable.

Active agents that were tested with some success in laboratory settings are heparin and hirudin derivatives, prostacyclins, corticoids, rapamycin, colchicine, and paclitaxel.

In most cases, the active agents were applied to stents; whenever solutions were used, these were aqueous solutions or, for the poorly water-soluble paclitaxel (4,10-β-diacetoxy-13-α-((2R,3S)-3-ben-zamido-2-hydroxy-3-phenylpropionyloxy)-2α-benzoyloxy-5-β, 20-epoxy-1,7-β-dihydroxy-11-taxene-9-one), aqueous solutions with an ethanol or cremophor additive. Micelles are formed when using cremophor [poly(oxyethylene)-35-castor oil] that can largely be avoided when using ethanol.

Suspensions or emulsions with relatively large-sized particles in aqueous cytostatic solutions with or without an added contrast agent have been described for direct injection into tumor-feeding blood vessels. These preparations are used to close tumor vessels and for simultaneous cytostatic treatment. Closing the vessels is directly opposed to the purpose of this invention.

It is the problem of this invention to provide agents for the local treatment of potentially hyperproliferative tissue that can be handled easily and do not harm the patient.

Based on the state of the art, this problem is solved according to the invention by a preparation containing at least one antihyperplastic agent with a distribution ratio between butanol and water of >0.5, and by inserting said preparation in an agent for enhancing the imaging of arteries and veins or by applying it to a catheter.

The concept of the invention is based on the observation that active agents from adequately concentrated solutions, gels or other matrices are absorbed fast and in sufficient quantities by a vessel wall unless they are enclosed in outwardly hydrophilic micelles by solubility promoters. When the active agents are lipophilic (butanol to aqueous buffer solution (pH 7) distribution ratio ≧0.5, preferably ≧1 and ≧5 particularly preferred, or octanol to aqueous buffer solution (pH 7) distribution ratio ≧1, preferably ≧10, and ≧50 particularly preferred), and/or reversibly (>10%, preferably >50%, >80% particularly preferred) and/or irreversibly bind to cell components (such as paclitaxel, probucol (4,4'-(isopropylidene-bisthio)bis(2,6-di-tert-butylphenol)), porphyrin derivatives), the retention time in the blood vessel when administered during vessel dilatation and optional stent implantation is sufficient for the treatment effect. Prevention or reduction of initial reactive hyperplasia as a consequence of vascular injury prevents the vessel wall from growing too thick over many months. Surprisingly, the preparations according to the invention did not require longer exposure of the tissue to be treated or indirect infiltration and additional injury of the vessel wall.

Contrast agents were selectively injected into the affected vessels several times during angioplasty and stent implantation to determine positioning, degree and form of the stenosis, to specify the exact position of the dilatation catheter, evaluate dilatation success, and, optionally, to implant a stent of appropriate thickness and length. By adding the active agents or their preparations that are suited for the purpose to the contrast agents used for diagnostic purposes, the active agent is transferred into the vascular wall with each injection of contrast agent, without additional effort or damage to the vessels. The entire vessel section imaged for diagnostic purposes is treated including the area in front of the stenosis and the area away from its center. This has the major benefit that critical zones upstream and downstream from the dilated stenosis and optional stent implantation are not excluded from treatment.

If the injection of contrast media is not required or undesirable, solutions of lipophilic active agents in other aqueous carriers can be used without adding micelle-forming substances. One requirement is that these solutions contain a higher active agent concentration than the saturation concentration in the aqueous medium. This can be achieved by adding organic solvents that form few or no micelles such as ethanol or DMSO and/or by dissolving the active agents under conditions that are not beneficial for storage and administration (e.g. heating, mixing with concentrated active agent solutions in organic solvents) to form sufficiently stable oversaturated solutions.

In some cases, solubility of the lipophilic active agents in the contrast agent solutions or the stability of oversaturated solutions are surprisingly improved. Another surprising effect due to the contrast agents is enhanced adhesion and absorption of active agents by vessel walls and good local tolerance of some substances of extreme systemic toxicity in sensitive vessel sections.

When active agent and contrast medium are incompatible or when the active agent does not dissolve properly in the contrast medium, the active agent solution can also be directly infused or injected through the diagnostic catheter into the respective vessel. It is preferred to use similar volumes as they are common for vessel imaging using contrast media through catheters [Elke M: Kontrastmittel in der radiologischen Diagnostik, pp. 113-119, 3rd edition, Georg Thieme Verlag Stuttgart New York, 1992].

Contrast agents are solutions, suspensions or emulsions well tolerated by vessels that can be used to enhance the representation of blood vessels or the bloodstream in radiograms, sonograms, optical imaging or magnet resonance imaging.

These contrast agents include Visipaque 320 (iodixanol), Ultravist 370 (iopromide), Omnipaque 350 (iohexyl) or Solutrast 370 (iopamidol) or Magnevist (gadolinium-DPTA) or Gadovist 1M (Gd-DO3A-butrol).

Active agents can be all substances suitable for inhibiting cell growth, cell multiplication and hyperplastic proliferation provided they meet the criteria defined above regarding lipophilia and/or binding to tissue components. Inasmuch as some active agents are not sufficiently lipophilic or capable of binding, their pharmacologically active derivatives or precursors of pharmacologically active substances may be used that release the actual active agent when in the tissue only. Preferred are cytostatics from the taxoid group such as paclitaxel and docetaxel ((2R,3S)—N-(tert-butoxycarbonyl)-2-hydroxy-3-phenyl-β-alan-ine-(4-acetoxy-2-α-benzoyloxy-5-β, 20-epoxy-1,7-β, 10-β-trihydroxy-9-oxo-11-taxene-13-α-yl-ester)), or epothilones as examples of lipophilic substances. These are so lipophilic and insoluble in water that even more hydrophilic derivatives as described by Nicollaou K C, Riemer C, Kerr M A, Rideout D, Wrasidlo W. Design, Synthesis and biological activity of protaxols. Nature, 1993; 364: pp. 464-466 or in U.S. Pat. No. 457,674, Novel Taxoids, are preferred as long as their molecular weight does not exceed ca. 10 kD.

Other useful active agents are selected from the groups of corticoids, mitosis inhibitors such as colchicine, antibiotics such as azithromycin or roxithromycin (Gupta et al. 1998) or antioxidants such as probucol, as well as heparin and hirudin derivatives or prostacyclins. Furthermore, immunosuppressants such as rapamycin are among the active agents that can be used.

Examples of lipophilic derivatives of otherwise hydrophilic cytostatics can be found in Brunner H, Schellerer K-M, Treittinger B. Synthesis and in vitro testing of hematoporphyrin type ligands in platinum(II) complexes as potent cytostatic and phototoxic antitumor agents. Inorganica Chimica Acta, 1997; 264: pp. 67-79 in the form of conjugates of platinum complexes with porphyrins.

The preparations according to the invention that contain a cytostatic as an active ingredient are also suitable for treating tumor diseases. It is advantageous in this case that the treatment is local, which minimizes the strain the patient is put under.

Besides lipophilic substances, other active agents or substrate-bound active agents with a specific affinity to vessel walls, particularly to vessel walls showing pathological change, are suitable. Substances have a specific affinity to vessel walls when they are not washed away by the bloodstream within a few minutes. It is known that small concentrations of magnetites are deposited after intravenous administration in vessel walls that show arteriosclerotic change (Schmitz S A et al. Superparamagnetic iron oxide—enhanced MRI of atherosclerotic plaques in Watanabe hereditable hyperlipidemic rabbits. Invest Radiol, 2000; 35: 460-471). However it is surprising that these magnetites reach concentrations sufficient for treatment after a short-time flow through the vessels that are dilated using a balloon. To make these magnetites usable for treatment, they must be coated with drugs as described, for example, by Lubbe A S, Bergemann C, Huhnt W. Fricke T, Riess H, Brock J W, Huhn D. Preclinical experiences with magnetic drug targeting: Tolerance and efficacy. Cancer Research, 1996, 56: 4694-4701).

The active agents are dissolved as much as possible in the undiluted contrast agents. They can also be prepared as a separate solution that is diluted with contrast agents prior to use. The mixing ratio of active agent solution and contrast agent solution should not be greater than 2:1, preferably <1:1, <0.2:1 being particularly preferred. The active agent should be dissolved in a well-tolerable aqueous medium or a medium that can be mixed with water. Also admissible are organic solvents that are well tolerated (at least after being diluted with the contrast agent solution or another aqueous medium) such as ethanol, DMSO, DMF, etc. The prepared injection solution will mostly contain as great a portion of water as possible (>90 volume percent, preferred >95 volume percent, >99 volume percent particularly preferred).

The concentration range of each active agent is dependent on their solubility in physiologically tolerable solvents without having to resort to micelle-forming agents such as cremophor and on the efficacy and tolerability of the active agents. The upper limit of the concentration is always determined by the volume to be administered (e.g. 100 to 200 ml for repeated injection into the coronary arteries) and the maximum systemically tolerable dose (e.g. ca. 100 mg per sqm body surface for paclitaxel). Preferred and sufficiently effective due to local administration and action are dosages of 1/10th or less of the maximum systemically tolerable dose.

Other effective substances such as coagulation inhibitors, platelet aggregation inhibitors, enzyme inhibitors, complex-forming agents for calcium ions, etc. may be added to the preparations. These do not have to meet the criteria for lipophilia, binding to tissue components or molecular weight as the effect can also be acute and intravascular; what has been said in the paragraph regarding concentration and dosage above applies here because the focus is on the local effect in the vessel section through which the preparation flows.

Another way of administering antiproliferative agents is provided by a catheter used for vessel dilatation that has an inflatable balloon which itself causes the vascular dilatation. The balloon can be coated with the active agent. When the vessel is dilated, the balloon is pressed against the vessel wall. This provides an opportunity for the active agent to transfer into the vessel wall. If the balloon is used to dilate a stent, even the active agent between the balloon and the stent can be released because the metal struts of the stent are displaced relative to the balloon surface. These variations of active agent administration do not constitute an additional step for the physician as compared to the original process of vessel dilatation or stent implantation.

The following methods can be used if the active agents are to be applied to the part of the catheter that is used for vessel dilatation: Dissolution of the active agent(s) in a solvent that does not corrode the catheter, immersion of the respective catheter part in the solution, removal of the catheter from the solution, and drying. Optionally, intravasally acceptable matrix or gel-forming adjuvants can be added to the active agent solution in the vessel, e.g. lipids or polymers used in pharmacology. Coating can be performed in several steps, while agent-containing and agent-free layers may alternate. The solvents for the respective layers should be selected in such a way that the subsequent coating does not strip off the previous one.

The examples below shall explain the invention:

EXAMPLES

Example 1a

Solution for Direct Administration into the Arteries 80 mg of 7-(2",3"-dihydroxypropyl oxycarbonyl)-paclitaxel are dissolved in 5 ml of dimethyl sulfoxide and diluted with 5 ml of a 5% glucose solution. The solution or a part thereof is slowly infused into the previously dilated arteries.

Example 1b

X-ray Contrast Medium with an Additive for Inhibiting Intimal Hyperplasia 99 parts of a portion of the solution described in 1a are added to the Visipaque 320, a commercial X-ray contrast medium, and immediately mixed well. The solution can be used as is common for angiography prior to or after vessel dilatation.

Example 2a

Solution as an Additive to Contrast Agents 200 mg of 7-(2",3"-dihydroxypropyl oxycarbonyl)-paclitaxel are dissolved in 10 ml of absolute ethanol (=solution A); 0.35 ml of this solution can be added to 100 ml of contrast agent.

Example 2b

X-ray Contrast Medium for Restenosis Prevention 100 ml of Ultravist 370 (Schering AG, Berlin; active ingredient iopromide equivalent to 370 mg of iodine/ml) containing 0.35 volume percent of ethanol and 7 mg of 7-(2",3"-dihydroxypropyl oxycarbonyl)-paclitaxel. The solution is produced by dissolving the 7-(2",3"-dihydroxypropyl oxycarbonyl)-paclitaxel in ethanol and adding it under constant stirring to the contrast agent.

Example 2c

X-ray Contrast Medium for Restenosis Prevention

The preparation according to Example 2b with an addition of 10 I.U. of low-molecular weight heparin.

Example 2d

Restenosis-Inhibiting Perfusion Solution 3.5 ml of the solution A described in Example 2a are mixed with 46.5 ml of ethanol and added under fast shaking to 1000 ml of warm (−50.degree. C.) 5% glucose solution or isotonic electrolyte solution. This solution is infused via a catheter into the vessels to be treated just like a contrast medium; however, the infusion rate can be reduced as compared to that of contrast agents.

Example 3a

X-ray Contrast Medium for Inhibiting Intimal Hyperplasia 100 ml of Ultravist 370 (see Example 2b) mixed with 0.4 volume percent of ethanol and 14.4 mg of 7-(2",3"-dihydroxypropyl oxycarbonyl)-paclitaxel. The preparation is produced as described in Example 2b.

Example 4a

X-ray Contrast Medium for Inhibiting Cell Growth 100 ml of Solutrast 370 (Byk-Gulden, Konstanz; active ingredient iopamidol equivalent to 370 mg of iodine/ml) containing 1.0 volume percent of ethanol and 8.2 mg of paclitaxel/ml. The preparation is produced by first dissolving the paclitaxel in absolute ethanol while heating it slightly, then adding the contrast agent quickly and under strong stirring.

Example 4b

X-ray Contrast Medium for Inhibiting Intimal Hyperplasia

Preparation according to Example 4a plus adding 5 I.U. of heparin and 5 mmol/l of citrate buffer (pH 7.0).

Example 5a

Solution as an additive to Contrast Agents or Infusion Solutions 20 mg of (±)-trans-1,2-diaminocyclohexane{7,12-bis[1-(1,4,7,10,1-3,16-hexaoxaheptadecyl)-ethyl]-3,8,13,17-tetramethylporphyrin-2,18-dipropionato}platinum(II) are dissolved in 10 ml of dimethyl sulfoxide (=solution B).

Example 5b

X-ray Contrast Medium with an Additive for Inhibiting Cell Growth 1 ml of solution B is added under fast stirring to 100 ml of Ultravist 370 (see Example 2b). The solution is suitable for infusion into arteries or injection into living or dead tissues or body cavities. It allows excellent control of its initial distribution and causes a long-lasting cytostatic effect.

Example 5c

Contrast Medium for Magnetic Resonance Tomography with an Additive for Inhibiting Cell Growth 1 ml of solution B is added to 10 ml of 50 mmolar gadolinium DTPA (=gadopentetate) solution. A 50 mmolar gadolinium-DTPA solution is prepared from Magnevist, a commercial preparation (Schering AG, Berlin), by diluting the product ten times. The solution can be infiltrated, for example, in vital tumors or in tumors after they were destroyed by ethanol, heat or cold treatment. The distribution of the solution is well visible in magnetic resonance tomograms. The solution itself supports the total destruction of the tumor in the immediately infiltrated area and its vicinity.

Example 6

In-Vivo Efficacy of the Preparation as Described in Example 2b 2 coronary arteries each in a total of 8 pigs were dilated under anesthesia, and stents (fine, heavily perforated metal tubes) were implanted. The arteries respond by wall thickening, which results in narrowing the original lumen of the arteries. 4 pigs were administered a regular X-ray contrast agent (Ultravist 370) for imaging the arteries and checking the stent implantation, 4 pigs were administered the preparation according to Example 2b. The vessels of both test groups practically had the same widths (inside diameters 3.4±0.2 mm and 3.5±0.2 mm) immediately after treatment. 4 weeks after treatment, the inside arterial diameter in animals that only received the regular contrast agent had stenosed by 1.9±0.8 mm, whereas the arterial diameter in the animals that were treated with the solution according to Example 2b was only reduced by 0.9±0.6 mm. This difference is statistically significant (p=0.01). The undiluted solution according to Example 2b was tolerated without side effects despite the addition of a high concentration of a relatively toxic cytostatic after injection in the coronary arteries and simultaneous ECG and blood pressure measurements.

Example 7a

Coating a Catheter

The distal area carrying the balloon of a balloon catheter designed for vessel dilatation is immersed under sterile conditions in the ethanolic solutions from Example 2a (=solution A), kept in the solution for ca. 5 minutes, then removed and dried for 2 hours at room temperature. The balloon catheter can then be used in the common way for dilating vessels.

Alternatively, a stent is placed on the balloon after drying.

Example 7b

The procedure is like in Example 7a, but 100 mg of pharmaceutical castor oil are now added to solution A.

Example 8a

Solubility in the Contrast Agent or Physiological NaCl Solution 7.6 mg of paclitaxel are dissolved in 0.5 ml of ethanol and added at room temperature to 50 ml Ultravist-370 (contains 768 mg of iopromide/ml, specific weight ca. 1.4 g/ml). A clear solution without any turbidity is obtained after mixing that remains stable for several days. No particles can be identified in the solution under a microscope.

4.2 mg of paclitaxel are dissolved in 0.5 ml of ethanol and added at room temperature to 50 ml of a 0.9% NaCl solution. The preparation becomes turbid immediately after mixing; most particles are found on the surface of the solution after 2 hours. Large aggregations of fine particles are found using a microscope.

Evaluation: The solubility of paclitaxel in the contrast agent is highly surprising. The contrast agent solution contains 0.7 ml of water/ml of solution mixture, i.e. Less solvent is available to paclitaxel in the contrast agent solution than in the NaCl solution. In spite of that, paclitaxel dissolves better in the contrast agent solution than in the NaCl solution.

Example 8b

Magnetite as the Carrier of the Antihyperplastic Agent 75 mg of paclitaxel are dissolved in 5 ml of ethanol. The paclitaxel solution is added to 50 ml of an aqueous preparation of a colloidal magnetite coated with degraded dextran (concentration refers to $Fe^{2+/3+}$ 0.5 molar, e.g. SH U 555C, test preparation by Schering AG, Berlin) and quickly intermixed. The magnetite particles adsorb paclitaxel and carry it after intravenous or intra-arterial injection, inter alia, into arterial walls showing arteriosclerotic change and brain tumors. Dosage depends on the use of the magnetite and is ca. 50 μmol referred to Fe/kg of body weight.

The invention claimed is:

1. A method for making a drug-coated angioplasty catheter, comprising:
    applying a solution of a lipophilic drug directly to a surface of a balloon wall of a balloon of an angioplasty catheter, and
    drying the solution to form a coating of the lipophilic drug directly on the balloon wall to provide an outermost surface over the balloon,
    wherein said solution comprises a solvent, said lipophilic drug, and a contrast agent, and said lipophilic drug is selected from azithromycin, roxithromycin, probucol, prostacyclins, corticoids, rapamycin, colchicine, paclitaxel, docetaxel, and 7-(2",3"dihydroxypropyl oxycarbonyl)-paclitaxel.

2. The method of claim 1, wherein the lipophilic drug is paclitaxel.

3. The method of claim 2, wherein the solution consists of said solvent, paclitaxel, and said contrast agent.

4. The method of claim 1, wherein the solution consists of said solvent, said lipophilic drug, and said contrast agent.

5. The method of claim 1, also comprising processing said angioplasty catheter to be suitable for insertion into a patient with said coating providing said outermost surface.

6. The method of claim 1, wherein said solvent is ethanol.

7. A method of claim 1, wherein said solution consists of ethanol, paclitaxel, and a contrast agent, and said applying is by immersing said balloon surface into said solution.

8. The method of claim 1, wherein said contrast agent is selected from iodixanol, iopromide, iohexyl, iopamidol, gadolinium-DPTA, and Gd-DO3A-butrol.

9. The method of claim 8, wherein the lipophilic drug is paclitaxel.

10. The method of claim 8, wherein the lipophilic drug is rapamycin.

11. The method of claim 1, wherein said contrast agent is selected from iodixanol, iopromide, iohexyl, and iopamidol.

12. The method of claim 9, wherein the lipophilic drug is paclitaxel.

13. The method of claim 11, wherein the lipophilic drug is rapamycin.

14. A method for making a drug-coated angioplasty device, comprising:
    applying a solution of a lipophilic drug directly to a surface of a balloon of an angioplasty device, said solution comprising a solvent, said lipophilic drug, and a contrast agent, and drying the solution to form a coating of the lipophilic drug directly on the surface of said balloon to provide an outermost surface over said balloon,
    wherein said lipophilic drug is selected from azithromycin, roxithromycin, probucol, prostacyclins, corticoids, rapamycin, colchicine, paclitaxel, docetaxel, and 7-(2", 3"-dihydroxypropyl oxycarbonyl)-paclitaxel.

15. The method of claim 14, wherein the lipophilic drug is paclitaxel.

16. The method of claim 15, wherein the solution consists of said solvent, paclitaxel, and said contrast agent.

17. The method of claim 14, wherein the solution consists of said solvent, said lipophilic drug, and said contrast agent.

18. The method of claim 14, also comprising rendering said angioplasty device suitable for insertion into a patient with said coating providing said outermost surface.

19. The method of claim 14, wherein said surface is a balloon wall surface of the angioplasty device.

20. The method of claim 14, wherein said contrast agent is selected from iodixanol, iopromide, iohexyl, iopamidol, gadolinium-DPTA, and Gd-DO3A-butrol.

21. The method of claim 20, wherein the lipophilic drug is paclitaxel.

22. The method of claim 20, wherein the lipophilic drug is rapamycin.

23. The method of claim 14, wherein said contrast agent is selected from iodixanol, iopromide, iohexyl, and iopamidol.

24. The method of claim 23, wherein the lipophilic drug is paclitaxel.

25. The method of claim 23, wherein the lipophilic drug is rapamycin.

26. A method for making an angioplasty device useful for applying a lipophilic drug to a wall of a vascular vessel of a patient, the angioplasty device comprising a balloon having an outermost surface for contact with the wall of the vascular vessel, the method comprising:
    processing an angioplasty device so as to be suitable for insertion into a patient to perform an angioplasty, wherein the processed angioplasty device comprises a balloon having an outermost coating comprising a lipophilic drug, the outermost coating positioned on a portion of the balloon that contacts the wall of the vascular vessel upon conduct of an angioplasty procedure with the angioplasty device;
    wherein said processing includes applying an amount of a solution comprising a solvent, said lipophilic drug, and a contrast agent directly to the balloon to form said outermost coating, and
    wherein said lipophilic drug is selected from azithromycin, roxithromycin, probucol, prostacyclins, corticoids, rapamycin, colchicine, paclitaxel, docetaxel, and 7-(2", 3"-dihydroxypropyl oxycarbonyl)-paclitaxel.

27. The method of claim 26, wherein said lipophilic drug is paclitaxel.

28. The method of claim 26, wherein the solution consists of said solvent, paclitaxel, and said contrast agent.

29. The method of claim 26, wherein the solution consists of said solvent, said lipophilic drug, and said contrast agent.

30. The method of claim 26, wherein said contrast agent is selected from iodixanol, iopromide, iohexyl, iopamidol, gadolinium-DPTA, and Gd-DO3A-butrol.

31. The method of claim 30, wherein the lipophilic drug is paclitaxel.

32. The method of claim 30, wherein the lipophilic drug is rapamycin.

33. The method of claim 26, wherein said contrast agent is selected from iodixanol, iopromide, iohexyl, and iopamidol.

34. The method of claim 33, wherein the lipophilic drug is paclitaxel.

35. The method of claim 33, wherein the lipophilic drug is rapamycin.

36. A method for making a drug-coated angioplasty catheter, comprising:
    applying a solution of a lipophilic drug directly to a surface of a balloon wall of a balloon of the angioplasty catheter and drying the solution to form a coating comprising the lipophilic drug directly on the balloon wall to provide an outermost surface over the balloon,
    wherein said solution comprises a solvent, said lipophilic drug, and a contrast agent, and said lipophilic drug is selected from azithromycin, roxithromycin, probucol, prostacyclins, corticoids, rapamycin, colchicine, paclitaxel, docetaxel, and 7-(2",3"-dihydroxypropyl oxycarbonyl)-paclitaxel.

37. A method for making a drug-coated angioplasty device, comprising:
    applying a solution of a lipophilic drug directly to a surface of a polymeric balloon wall of a balloon of an angioplasty device and drying the solution to form a coating of the lipophilic drug directly on the polymeric balloon wall to provide an outermost surface over the balloon, wherein said solution comprises a solvent, said lipophilic drug, and a contrast agent, and said lipophilic drug is selected from azithromycin, roxithromycin, probucol, prostacyclins, corticoids, rapamycin, colchicine, paclitaxel, docetaxel, and 7-(2",3"-dihydroxypropyl oxycarbonyl)-paclitaxel.

* * * * *

UNITED STATES PATENT AND TRADEMARK OFFICE
CERTIFICATE OF CORRECTION

PATENT NO. : 8,389,043 B2
APPLICATION NO. : 12/835420
DATED : March 5, 2013
INVENTOR(S) : Speck et al.

It is certified that error appears in the above-identified patent and that said Letters Patent is hereby corrected as shown below:

ON THE TITLE PAGE:

Item (57), under "ABSTRACT", in Column 2, Line 7, delete ".gtoreq.0.5." and insert -- $\geq 0.5$. --, therefor.

IN THE SPECIFICATION:

In Column 3, Line 67, delete "(iohexyl)" and insert -- (iohexol) --, therefor.

In Column 5, Line 7, delete ">99" and insert -- $\geq 99$ --, therefor.

In Column 8, Line 60, delete "dextran" and insert -- dextrane --, therefor.

IN THE CLAIMS:

In Column 9, Line 30, in Claim 8, delete "iohexyl," and insert -- iohexol, --, therefor.

In Column 9, Line 37, in Claim 11, delete "iohexyl," and insert -- iohexol, --, therefor.

In Column 9, Line 38, in Claim 12, delete "claim 9," and insert -- claim 11, --, therefor.

In Column 9, Line 66, in Claim 20, delete "iohexyl," and insert -- iohexol, --, therefor.

In Column 10, Line 6, in Claim 23, delete "iohexyl," and insert -- iohexol, --, therefor.

In Column 10, Line 39, in Claim 30, delete "iohexyl," and insert -- iohexol, --, therefor.

In Column 10, Line 46, in Claim 33, delete "iohexyl," and insert -- iohexol, --, therefor.

Signed and Sealed this
Fourth Day of June, 2013

Teresa Stanek Rea
*Acting Director of the United States Patent and Trademark Office*

Adverse Decision in Interference

Patent No. 8,389,043, Ulrich Speck and Bruno Scheller, PREPARATION FOR RESTENOSIS PREVENTION, Interference 106,044, final judgment adverse to patentees rendered, February 18, 2016, as to claims 1-37.

*(Official Gazette March 24, 2020)*